United States Patent [19]

Wieboldt et al.

[11] Patent Number: 4,914,297

[45] Date of Patent: Apr. 3, 1990

[54] INFRARED SPECTROMETER INTERFACE FOR THERMOGRAVIMETRIC ANALYSIS

[75] Inventors: Richard C. Wieboldt, Verona; Gregory E. Adams, Madison, both of Wis.

[73] Assignee: Nicolet Instrument Corporation, Madison, Wis.

[21] Appl. No.: 137,452

[22] Filed: Dec. 23, 1987

[51] Int. Cl.⁴ .................................... G01N 21/01
[52] U.S. Cl. ............................ 250/343; 356/246
[58] Field of Search .................. 250/343, 432 R; 356/244, 246

[56] References Cited

U.S. PATENT DOCUMENTS

| | | | |
|---|---|---|---|
| 3,307,447 | 3/1967 | Carleton et al. | 356/246 |
| 3,515,491 | 6/1970 | Emary | 356/246 |
| 3,524,066 | 8/1970 | Blakkan | 250/576 |
| 3,524,709 | 8/1970 | Hrdina | 356/246 |
| 3,556,659 | 1/1971 | Hawes | 356/301 |
| 3,567,329 | 3/1971 | Willis et al. | 356/246 |
| 3,583,817 | 6/1971 | Rachlis et al. | 356/410 |
| 3,588,496 | 6/1971 | Snowman | 250/343 |
| 3,792,272 | 2/1974 | Harte et al. | 250/343 |
| 3,920,334 | 11/1975 | Steichen et al. | 356/73 |
| 3,940,623 | 2/1976 | Hempowitz et al. | 250/343 |
| 4,033,699 | 7/1977 | Bayly et al. | 356/436 |
| 4,156,143 | 5/1979 | Adrian | 250/343 |
| 4,209,232 | 6/1980 | Chernin | 350/619 |
| 4,226,532 | 10/1980 | Berber et al. | 356/336 |
| 4,286,873 | 9/1981 | Carson | 356/130 |
| 4,405,235 | 9/1983 | Rossiter | 356/246 |
| 4,440,013 | 4/1984 | Adams | 73/23.1 |
| 4,455,089 | 6/1984 | Yeung et al. | 356/352 |
| 4,575,424 | 3/1986 | Allington et al. | 210/198.2 |
| 4,587,835 | 5/1986 | Adams | 73/23.1 |
| 4,588,893 | 5/1986 | Vidrine et al. | 250/428 |
| 4,618,771 | 10/1986 | Farren | 250/343 |
| 4,632,563 | 12/1986 | Lord, III | 356/437 |

OTHER PUBLICATIONS

Peter R. Griffiths, "Fourier Transform Infrared Spectrometry," Science, vol. 222, Oct. 21, 1983, pp. 297–302.
C. A. Cody et al., "Evolved Gas Analysis (EGA) via Fourier Transform Corporation," FT-IR Application Note 8308.
John O. Lephardt et al., "Fourier Transform Infrared Evolved Gas Analysis: Additional Considerations and Options," Applied Spectroscopy, vol. 35, No. 1, 1981, pp. 95–101.
D. A. C. Compton et al., "The Use of a Small Low-Cost FT-IR Spectrometer as a Mobile Analyzer for Fluid Streams," Applied Spectroscopy, vol. 39, No. 6, 1985, pp. 909–915.
Luis A. Sanchez, "Fourier Transform Infrared Analysis of Evolved Gases in Polymerization and Pyrolysis Processes," Applied Spectroscopy, vol. 41, No. 6, 1987, pp. 1019–1023.

Primary Examiner—Constantine Hannaher
Attorney, Agent, or Firm—Lathrop & Clark

[57] ABSTRACT

A thermogravimetric analysis flow cell interface unit has an elongated tubular cell body, glass inlet and outlet transfer lines integrally connected to the cell body for flowing a gas therethrough, a window element for allowing passage of an infrared radiation beam into and out of the cell body, and a mirror element for reflecting the radiation beam back through the cell body. The mirror element and the window element are assembled to the cell body in such a manner that the entire unit may be quickly disassembled and reassembled for easy cleaning and replacement. The flow cell assembly is adapted to interface a thermogravimetric analyzer and an infrared spectrometer.

9 Claims, 5 Drawing Sheets

INFRARED SPECTROMETER INTERFACE FOR THERMOGRAVIMETRIC ANALYSIS

TECHNICAL FIELD

This invention pertains generally to the field of spectrometry and particularly to an interface system for combining thermogravimetric analysis and infrared spectrometry.

BACKGROUND OF THE INVENTION

Thermogravimetric analysis (TGA) is a widely established technique for measuring the change in weight of a sample as a function of temperature or time in a controlled atmosphere. The change in weight is usually accompanied by the evolution of gases caused by sample decomposition or evaporation. TGA is used to study the thermal stability of materials, decomposition kinetics, and moisture and volatiles content as well. However, TGA does not have the ability to identify gaseous components evolved during the weight loss. The identification of the gaseous components in these off-gases would be beneficial in determining sample characteristics such as decomposition pathways or thermal stability.

Infrared Spectrometry (IR) is used extensively in areas of gas analysis because it is a relatively convenient technique and provides positive identification of gases. For example, IR spectrometry is used in applications such as gas chromatographic (GC) infrared analysis to identify vapor phase materials. In GC/IR spectrometry, a gaseous sample is passed through a flow cell analyzer, also known as a light pipe. The various constituents of the sample flow from the GC at different times. Infrared radiation energy from an interferometer is directed through the light pipe and is absorbed by the constituents in a manner which determines the quantity and type of constituent. The infrared radiation from the sample is then directed into a detector. In the course of operation, the interferometer includes a movable mirror which reciprocates back and forth and produces interference within the infrared radiation so that during each scan or movement of the mirror, the output of the detector produces an interferogram. This output is an electrical signal in analog form that is then amplified and digitized in the electronic system and fed into a data system where it undergoes a Fourier transform and is analyzed. A description of Fourier transform infrared spectrometer (FTIR) systems may be found in Griffiths, Peter R., "Fourier Transform Infrared Spectrometer", *Science*, Vol. 222, pp. 297-302, 21 October 1983, the contents of which are incorporated herein for an explanation of the FTIR system.

A typical light pipe accessory used in FTIR includes a hollow glass tube with infrared transparent windows sealed at either end of the tube. Infrared transmissive "salt" windows, e.g., windows made of potassium bromide or zinc selenide, are mounted to both ends of the light pipe using seals to seal off the bore of the light pipe to prevent escape of the gases. The characteristics of the light pipe are crucial to the performance of the system. It is generally desirable to maximize the number of sample molecules that are in the infrared beam path while minimizing the radiation loss due to reflection and absorbence. Material in the light pipe which contacts the gas must also be non-reactive. The light pipes used in commercial instrumentation to meet these requirements are typically cylindrical glass tubes having a small internal diameter on the order of 1 to 3 mm and which have a thin coating of gold deposited on the inner surface. Gold is used because it is reflective, stable and inert.

In the past, the TGA and FTIR analysis systems were used independently and often by separate operators in different laboratories. This, however, has proved to be an inefficient means for providing a complete sample analysis, or for measuring quantitative weight loss and identifying evolved gases.

SUMMARY OF THE INVENTION

The flow-through gas cell unit of the present invention overcomes the problems described above by providing a system for combining a TGA unit with an IR or FTIR unit to provide a complete sample analysis system. The invention is directed to a heated flow-through thermogravimetric analysis/infrared (TGA/IR) gas cell interface assembly for use in examining, with infrared radiation, the evolved gas from a TGA system. The entire interface assembly is constructed to work as a separate unit that can easily be placed into or taken out of the analysis system.

The TGA/IR flow cell apparatus generally comprises an elongated tubular glass cell body having two ends. The first end includes a window unit for allowing the passage of an infrared radiation beam into and out of the cell body. The second end includes a mirror unit for reflecting the radiation beam, which enters the cell body via the window unit, back through the window unit. Thus, the length of the infrared beam in the flow cell apparatus is effectively doubled. Additionally, substantially all of the infrared beam passing through the window unit into the flow cell body is reflected by the mirror unit out of the window unit for analysis. The flow cell apparatus also includes inlet and outlet gas transfer lines connected to the cell body near the opposite ends thereof for flowing a gaseous sample therethrough. The inlet line is readily connectable to a line leading from the hot gas source of the TGA system. The outlet line is connected to an exhaust system. The TGA/IR interface unit is readily adapted to be inserted in the path of the infrared beam in the IR sample compartment.

The flow cell assembly of the present invention further has the advantage that the cell body, the transfer lines and all portions exposed to the sample gases are contained in a single removable assembly, providing easy interchanging of interface cell units between experiments.

It is a major advantage of the present invention that only a single window is required in the TGA/IR interface assembly, because salt windows, i.e., windows made from potassium bromide or zinc selenide, are expensive, require frequent cleaning, and are relatively fragile and easily damaged. Additionally, the mirror, which replaces a window at one end of the flow cell assembly, is relatively less expensive than a salt window, easier to replace, and easier to clean. Further, the infrared beam traverses the cell body twice as a result of being reflected off the mirror, which doubles the amount of absorption by the analyte gas. The optics of the assembly are preferably so arranged that the infrared beam does not reflect off the interior walls of the flow cell. Thus, the beam is not affected by any contamination on the interior wall surface and the loss of beam energy that would occur at such internal reflections is avoided.

The composition of the inlet and outlet transfer lines and their method of attachment to the flow cell body result in further advantages to the system. These lines conduct a sample gas from the end of the TGA furnace tube to the flow cell body and back out of the cell body to a room vent. The transfer lines are integrally connected to the cell body and are made from the same or similar chemically inert glass as the cell body. Because the inlet and outlet lines are integral with the cell body and are made from the same material, there are no problems encountered with the differential expansion and contraction rates which often occurs with prior art systems utilizing metal inlet and outlet lines connected to a glass flow cell tube. The positions of the inlet and outlet transfer lines are also designed for the most efficient exchange of gases within the cell.

Further objects, features, and advantages of the invention will be apparent from the following detailed description when taken in conjunction with the accompanying drawings.

DESCRIPTION OF THE PREFERRED EMBODIMENT

Figure 1:
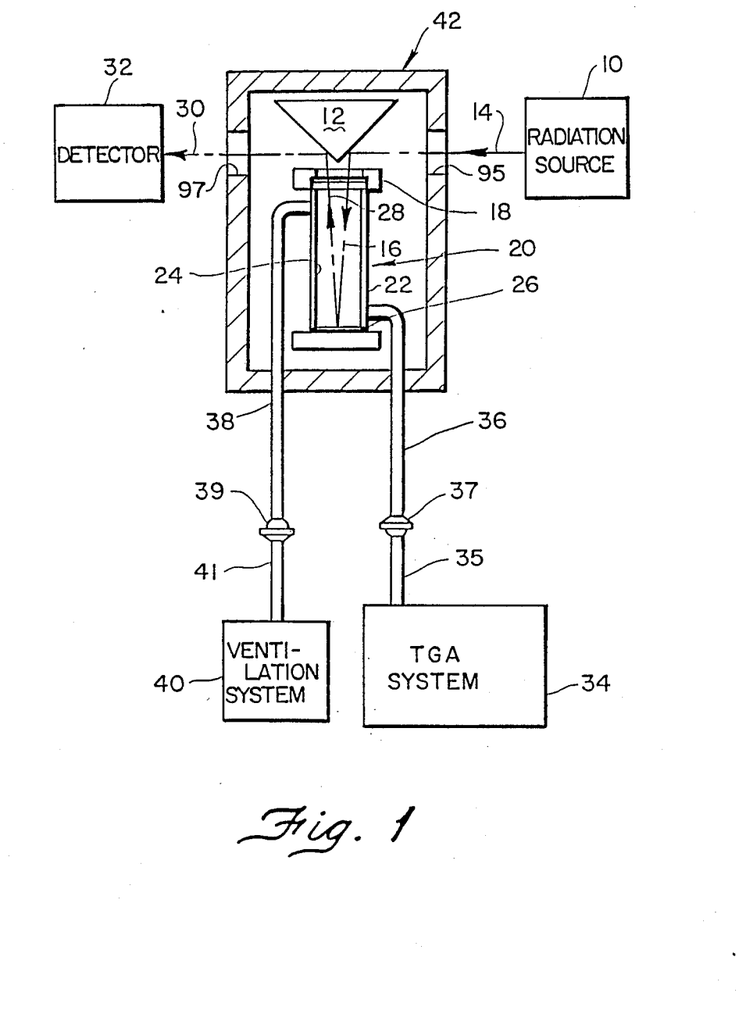
FIG. 1 is a schematic diagram of a TGA/IR sampling apparatus in accordance with the present invention.

With reference to the drawings, a TGA/IR sampling apparatus incorporating the present invention is shown generally in schematic form in FIG. 1. The apparatus includes a radiation source 10, e.g., a conventional source of infrared radiation for FTIR spectrometric analysis, and a system of transfer optics 12 which manipulates a radiation beam 14 from the source 10 and produces an input beam 16. The input beam 16 is focused upon the window element 18 at the beam transmission end of a flow cell assembly, generally referred to by reference numeral 20. The flow cell assembly includes a flow cell body 22 to which the window element 18 is attached at one end. The cell body 22 has an internal bore 24 preferably, although not necessary, circular, through which the input beam 16 is passed. At the other end of the cell body 22 is a mirror element 26 which serves to reflect the input beam back through the window element 18 on an output beam path 28. The transfer optics 12 again manipulates the output beam 28 to direct the beam, via pathway 30, to a detector 32 for analysis. In addition, a TGA system 34 produces a sample effluent stream which is directed into the bore 24 via an inlet transfer line 36 to allow the analytical radiation beams 16 and 28 to pass through the effluent stream within the bore 24. After passing through the bore 24, the effluent is exhausted via an outlet transfer line 38 to a proper ventilation system 40. The flow cell assembly 20 and the system of transfer optics 12 are preferably housed within an oven compartment 42 which will provide a properly heated environment sufficient to substantially prevent any condensation on optical surfaces which might otherwise result from the transfer of the hot effluent gases from the TGA system 34 to the cell body 22.

The present invention is particularly useful in infrared analysis systems such as are found in Fourier transform infrared (FTIR) spectrometers. A variety of infrared sources are commercially available and can be chosen to cover the wavelengths desired. Common detectors for infrared radiation include deuterated triglyceride sulfate (DTGS), pyroelectric bolometers and mercury cadmium telluride (MCT) detectors.

Figure 2:
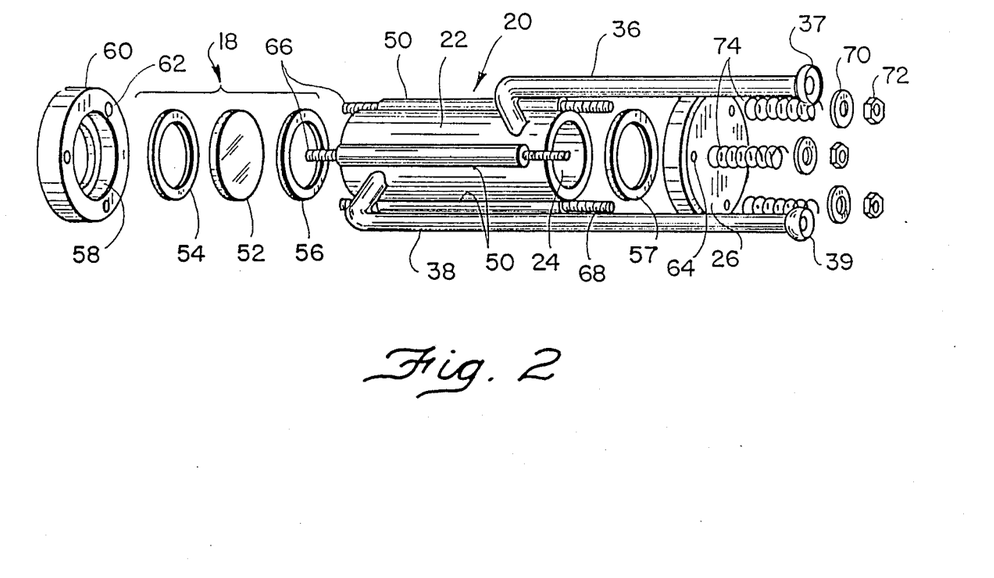
FIG. 2 is an exploded perspective view of a TGA/IR interface unit in accordance with the present invention.

A more detailed exploded view of the flow cell assembly 20 is shown in FIG. 2. The flow cell assembly 20 includes a generally circular cell body 22 bordered at one end by the window element 18 and at the other end by the mirror element 26. The window element 18 and the mirror element 26 are releasably secured to the ends of the cell body 22 by means of three support rods 50. It is understood that more or fewer support rods 50 may be included for the purpose of securing the window element 18 and the mirror element 26 to the cell body 22. The inlet and outlet transfer lines 36 and 38, respectively, are attached to the cell body 22 such that the channels of the inlet and outlet transfer lines communicate directly with the internal bore 24 of the cell body 22. The cell body 22, the transfer lines 36 and 38, and all portions exposed to evolved gases are contained in a single removable assembly, which has been referred to herein as the flow cell assembly 20.

In accordance with the present invention, the cell body 22 generally includes a hollow glass tube. The characteristics of the cell body 22 are crucial to the performance of the system. It is generally desirable to maximize the number of sample molecules that are in the infrared beam path while minimizing the radiation loss due to reflection and absorbance. Thus, the material in the bore 24 of the cell body 22 which contacts the gas must be non-reactive. In view of the manner in which the infrared beam is transmitted through the cell body, which will be more thoroughly described hereinafter, the cell body does not necessarily have to have a reflective coating on its inner surface. The glass cell body may be surrounded and protected by a support or holder (not shown) typically formed of a metal, such as stainless steel.

Due to the multiple passage of the infrared beam through the length of the cell body to obtain maximum signal modulation from the gas flowing through the cell, the length of the cell body 22 may be considerably shorter than standard flow cell bodies of the prior art. For example, a cell body of the present invention may be formed of a precision bored silica glass tube having a length of about 100 mm and an internal bore preferably about 25.4 mm in diameter, although larger and smaller bore flow cells may be utilized in accordance with the principles of the present invention. The manner of making the bore of the cell body is well known in the art and may be done in any desired manner.

The flow cell assembly 20 is sealed at one end by the window element 18. The window element 18 includes a window 52 bordered on either side by elastomeric sealing rings 54 and 56 (e.g., formed of a fluoro-polymer sold under the name Fluorolor-K by the Fluorocarbon Company) and nested within the well 58 of the window holder 60. The window 52 is an infrared transmissive window, for example, formed of potassium bromide or zinc selenide, preferably having a thickness of about 2 mm. The window 52 preferably combines the characteristics of substantial transparency to infrared radiation and good structural strength. It is a major advantage of the present invention that only a single window is required since "salt" windows, i.e., windows made of potassium bromide or zinc selenide, are expensive, require cleaning, are relatively fragile and are easily damaged.

Figure 3:
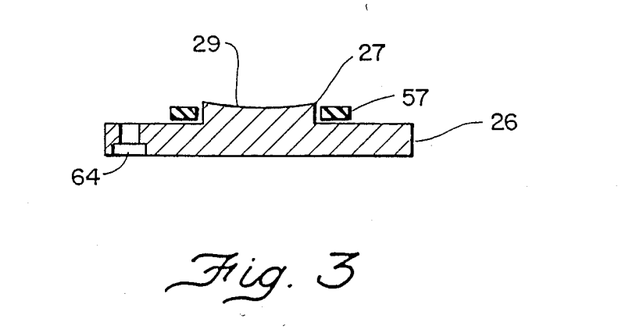
FIG. 3 is a cross-sectional view through the mirror element of the sampling apparatus.

The other end of the cell body 22 is bordered by the mirror element 26 which includes a mirror 27 having a spherical mirror surface 29, as shown in cross-section in FIG. 3) facing the window 52. The mirror is made of a metal or ceramic material, e.g., aluminum, and is coated with durable material which is highly reflective of infrared radiation, such as nickel, to reflect the infrared beam which has entered the cell body 22 back through the window 52. The mirror may be multiply coated, for example with a base layer of nickel for durability and an outer layer of gold for chemical inertness and infrared reflectivity. An elastomeric sealing ring 57 is also provided between the cell body 22 and the mirror element 26 to sealingly engage the mirror element 26 to the cell body 22 when the entire flow cell assembly 20 is assembled. By the action of the elastomeric sealing rings 54, 56 and 57, seated respectively on either side of the window 52 and between the cell body 22 and the mirror element 26, the internal bore 24 of the cell body 22 is effectively sealed off from the ambient atmosphere when the flow cell assembly 20 has been properly assembled.

The inlet transfer line 36 and outlet transfer line 38 are both preferably formed of non-reactive glass tubes, similar to the material of the cell body 22, and are integrally fused to the cell body 22. Thus, the inlet and outlet transfer lines 36 and 38 form a single unit with the cell body 22 which can be maintained within the oven compartment 42. Because the inlet and outlet transfer lines 36 and 38 are integral with the sample cell, problems encountered in conventional prior flow cells with differential expansion and contraction rates of a glass tube flow cell and metal inlet and outlet lines are avoided. Thus, the whole flow cell assembly 20 is constructed to work as a unit which can easily be inserted in the path of an infrared beam in the spectrometer sample compartment. The glass inlet and outlet transfer lines 36 and 38 lead to connectors 37 and 39, respectively, positioned outside the oven where they will be at a lower temperature and can readily interface with the normal supply and exhaust lines. The inlet transfer line 36 is readily connectable to an output line 35 leading from the gas source. The inlet line 36 is preferably connected through a ball and socket joint (the connector 37 forming the socket) to the line 35 leading from the hot gas source, i.e., the TGA system 34 illustrated in FIG. 1. As explained further below, the inlet line is passively heated by superheated gases flowing from the TGA furnace tube and by heat transfer from the furnace tube itself which is attached directly to the side arm using a ball and socket connection. The passive heating of the inlet line permits portions of excess evolved material to condense before having a chance to foul the window 52 or mirror surface 29.

The window element 18 and the mirror element 26 are provided with apertures 62 and 64, respectively, for releasably receiving the support rods 50. The support rods 50 are provided with threads 66 so that the rods can be threaded into the apertures 62. The other ends, i.e., the mirror ends, of the support rods 50 are also provided with threads 68. The support rods are mounted onto the mirror element 26 by any attachment means suitable to the art. In a preferred embodiment of the present invention, the apertures 64 are not threaded, thereby allowing the threaded portion 68 of the support rods 50 to freely traverse the apertures 64. As shown in FIG. 2, the attachment means may preferably be a washer 70 and nut 72 combination which threadably receives the threaded portion 68 of the support rod 50. It is also preferred that a spring 74 be provided on the threaded portion 68 of each of the support rods 50 between the mirror element 26 and the nut 72. The spring 74 is calibrated to provide the correct sealing force to the entire flow cell assembly 20 when the washers 70 and nuts 72 are flush with the back surface of the mirror element 26 and thereby provide a relatively constant sealing pressure throughout the range of temperatures to which the assembly is subjected, despite different expansion rates for the glass and metal parts.

Figure 5:
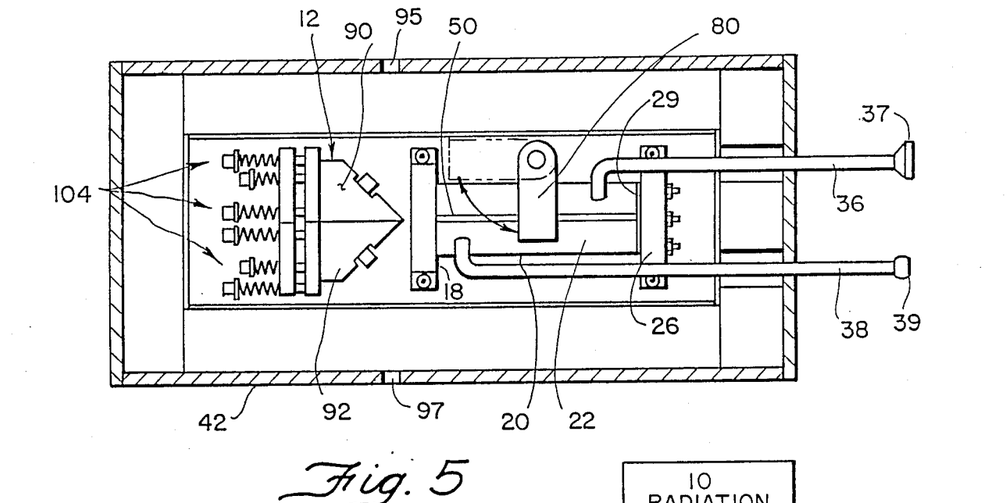
FIG. 5 is a top view of the TGA/IR interface illustratively shown in an oven compartment.

Referring now to FIG. 5, the manner in which the flow cell apparatus is inserted into the oven compartment 42 will now be described. The flow cell assembly 10 is adapted to mount in a standard center-focus cell compartment which uses standard infrared detector methods. The flow cell assembly is preferably mounted on two alignment pins (not shown) in the insulated oven compartment 42. A spring-loaded retaining bar 80 is designed to clamp down over the top supporting rod 50 of the cell assembly 20. When the retaining bar 80 is in place, it firmly holds the cell body 22 in correct optical alignment relative to a set of transfer optics 12. Thus, because the cell body 22 is held in optical alignment by a set of alignment pins, the design makes it easy to switch cells between experiments, and does not require further optical alignment.

The oven compartment 42 is an insulated heating chamber which maintains the flow cell assembly 20 at any preselected temperature, preferably from ambient temperature to 325° C. During the operation of the system, various heaters (not shown) which may be of conventional design are energized to bring the desired operating parts to proper temperature. The operation includes adjusting the heater so that the temperature in the flow cell 20 is sufficiently high to prevent the condensation of any gas therein.

The glass inlet and outlet transfer lines 36 and 38 lead to positions outside the oven compartment 42 where they will be at a lower temperature and can readily interface with normal supply and exhaust lines (shown as lines 35 and 41, respectively, in FIG. 1). The inlet transfer line 36 is designed to attach directly to the furnace tube of a TGA furnace unit by a simple ball and socket connection or other means known to the art. The outlet transfer line 38 is conveniently connected to any exhaust system known to the art.

Figure 4:
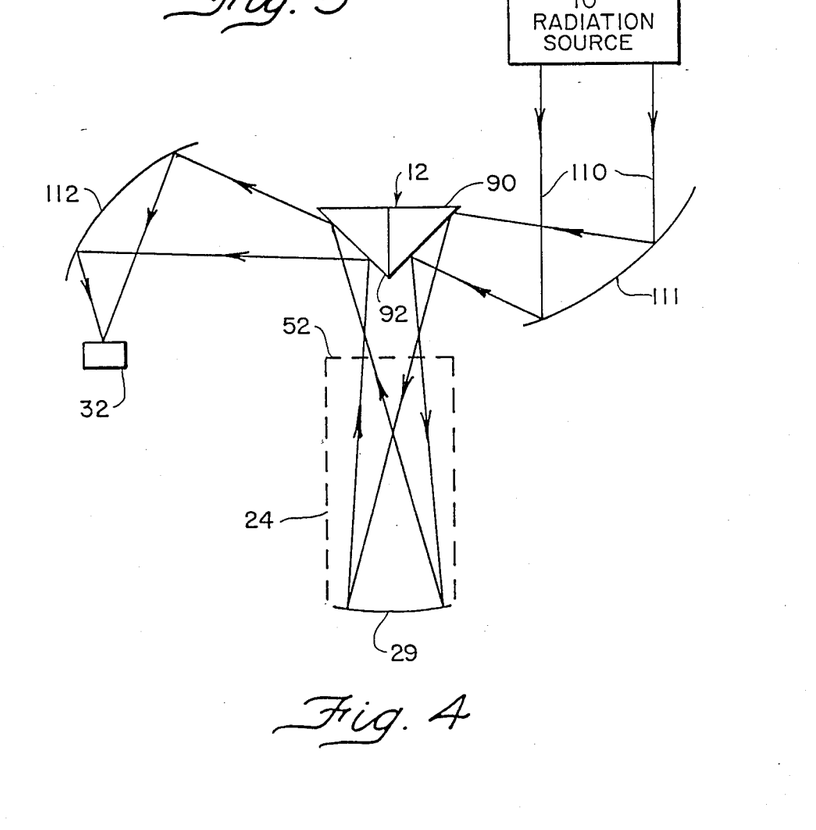
FIG. 4 is a schematic view showing the preferred arrangement of the optics in the sampling apparatus.

Referring to FIGS. 1, 4 and 5, the flow cell assembly 20 is adapted to be used with a radiation source 10 and a system of transfer optics 12 which produces a focused output beam 16. The optics system 12 includes a 90° prism which includes two symmetrical 90° deflectors. The first deflector, referred to as the input optics 90, directs the infrared beam 14 in an optical path 16 through the window element 18 into the internal bore 24 of the cell body 22 to the mirror element 26. The mirror element 26 reflects the infrared beam back through the internal bore 24, via path 28, to the collection optics 92 which deflects the beam, containing the required information, to a detector 32, via path 30, for analysis by methods known to the art. Thus, the infrared beam of the present invention sees only the gas in the cell body 22, the window 52 and the mirror element 26. Any material condensing on the internal bore wall 24 of the cell body 22 does not interact with the infrared beam. As a result, the output of the analyzer may be more stable than the outputs of analyzers having flow cell bodies that have highly polished inner surfaces that reflect the beam. As best illustrated in the schematic view of FIG. 4, the source 10 preferably provides a modulated collimated beam 110 which is reflected from a parabolic focusing mirror 111 (e.g., with a 152.4 mm focal length) onto the deflector 90, with the beam coming to a focus at about the position of the window 52 (illustrated in dashed lines in FIG. 4). After passing through the window, the diverging beam traverses the length of the flow cell without contacting the wall of the bore 24 and is reflected from the spherical mirror surface 29 (e.g., 100 mm radius) which has a focal length such that the reflected beam comes to a focus at about the position of the window 52. After passing through the window, the diverging beam is reflected from the deflector 92 onto an elliptical focusing mirror 112 which focuses the beam onto an infrared detector 32.

Figure 6:
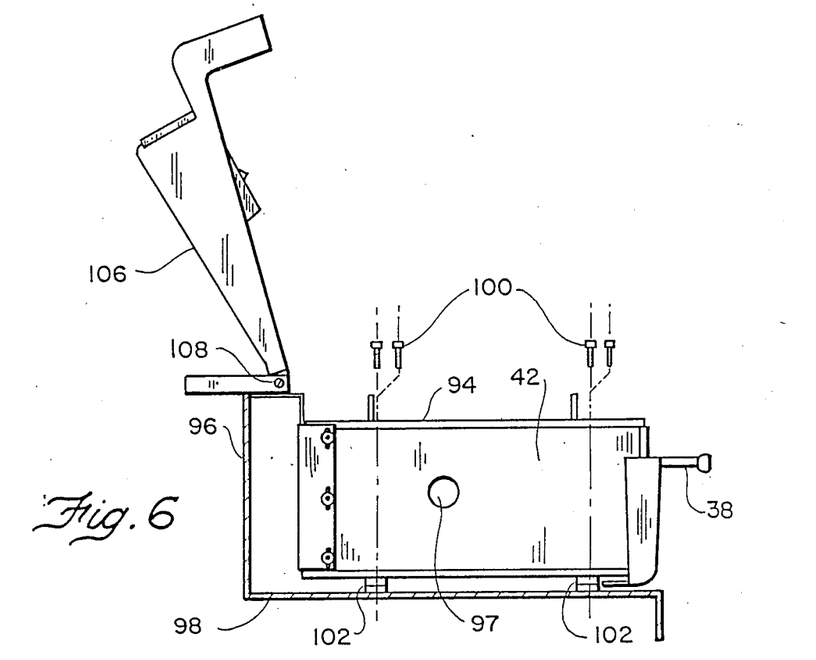
FIG. 6 is a side elevation view of the oven compartment of FIG. 5 in open position.
Figure 7:
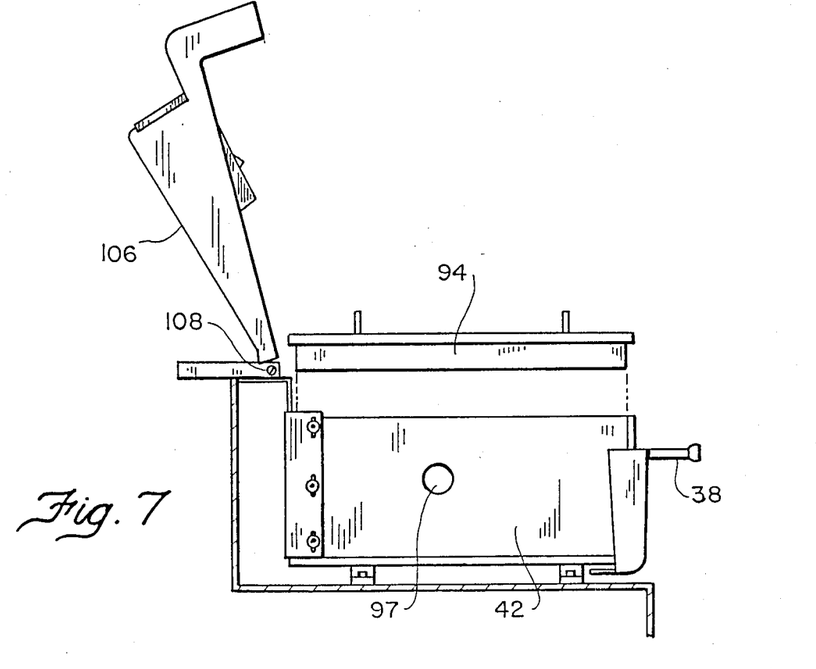
FIG. 7 is a side elevation view of the oven compartment of FIG. 6 shown illustratively mounted in a spectrometer.

Referring now to FIGS. 6 and 7, an insulated cover plate 94 fits into the oven compartment 42 to keep the cell assembly 20 hot while shielding the detector 32 from excess heat. The infrared beam from the source enters the oven compartment through an aperture 95 and exits to the detector through an aperture 97. The oven compartment 42 fits into a spectrometer sample compartment 96. The oven compartment 42 is releasably secured to the base plate 98 of the sample compartment 96 by, for example, four screws 100, which secure the oven compartment 42 to the base plate 98 of the sample compartment on raised studs 102. The position of the studs 102 on the base plates 98 ensures that the oven compartment 42 will mount in correct optical alignment in relation to the spectrometer optics system. Final optical adjustments can be made according to methods known in the art, such as using fine alignment screws 104 on the cell input and collection optics 90, 92, as illustrated in FIG. 5. A cover 106 is lowered over the entire assembly during operation. As illustrated in FIGS. 6 and 7, the cover 106 may be hingedly mounted at 108 to a structural member of the IR spectrometer.

In accordance with the operation of the present invention, heat is applied to the entire flow path from the inlet transfer line 36, cell body 22, window 52, and mirror element 26, up to the outlet transfer line 38 to prevent condensation of gaseous materials. This is achieved by actively heating the flow cell assembly 20 in the insulated oven compartment 42 using a temperature regulated heating unit (not shown) of conventional design. The inlet transfer line 36 is passively heated by superheated gases flowing from the TGA furnace tube and the furnace tube itself, which is attached directly to the inlet transfer line 36. The outlet transfer line 38 is not actively heated. This line is downstream from the infrared analysis position and as the gaseous materials are no longer needed, they can be safely trapped in this cooler transfer line.

The flow cell assembly 20 of the present invention is readily and easily adaptable for placement as a TGA-/IR interface unit in infrared spectrometers and connected to thermogravimetric analyzers known to the art. The TGA/IR interface is unique in that the cell body 22, transfer lines 36, 38 and all portions exposed to the evolved gases are contained in a single removable assembly. Therefore, no modifications to either the TGA furnace system or the FTIR spectrometer are required.

The types of samples analyzed by the flow cell assembly of the present invention are extremely varied due to the flexibility of the TGA system. Thus, it is difficult to describe the operation of the TGA/IR interface without some generalization. In most cases, however, the gaseous components evolved during a typical TGA experiment can be thought of as falling into two categories, those released before and after sample decomposition. Generally, the first category of components is of primary interest and tends to have a lighter molecular weight due to entrained solvents, plasticizers, etc. During sample decomposition, large volumes of material are expelled. This evolution is a mixture of decomposition products and is usually accompanied by particulates. Portions of this material invariably condense in cooler portions of the flow system. This typically shows up as a discoloration at the end of the TGA furnace tube.

The TGA/IR interface unit of the present invention particularly addresses the problem of handling large quantities of material released during sample decomposition. First, the inlet transfer line 36, which is attached to the TGA furnace tube, is not actively heated. This permits a portion of the incoming material, e.g., the heavier molecular weight bulk material, to condense before having a chance to foul the cell optics. Lighter components which are generally the ones of interest and evolve before the bulk decomposition are successfully carried through this zone without condensation. Second, the infrared beam does not "see", i.e., reflect off, the walls of the flow cell. As a result, any materials which condense on the walls do not contribute to the infrared spectrum. The only surfaces where condensed material may need to be removed are the interior face of the salt window and the cell mirror. Both are easily cleaned by disassembling the cell and can be economically replaced. Third, the cell body is a separate assembly which can be quickly inserted in or removed from the heated chamber. This feature allows easy exchange of cells between experiments.

It is understood that the invention is not confined to the particular embodiment and examples herein illustrated and described, but embraces such modified forms thereof as come within the scope of the following claims.

What is claimed is:

1. A flow-through gas cell unit for use in infrared spectrometry, comprising:
   (a) an elongated tubular glass cell body having first and second ends and a wall defining an internal bore;
   (b) glass inlet and outlet transfer lines integrally fused to the cell body to form a single unit, the inlet and outlet transfer lines having channels for flowing a gas therethrough which communicate with the internal base of the cell body;
   (c) a window element for allowing passage of a radiation beam into and out of the cell body, the window element mounted at the first end of the cell body; and (d) a mirror element for reflecting the radiation beam, the mirror element mounted at the second end of the cell body such that substantially all of the radiation beam passing into the window element of the cell body is reflected by the mirror element out of the window element for analysis, wherein the window element and mirror element are releasably secured to the ends of the cell body by support rods extending between the window element and mirror element.

2. The gas cell unit of claim 1 wherein the support rods include a spring mechanism in order to provide a sealing force appropriate to sealingly engage the window element and mirror element to the cell body.

3. The gas cell unit of claim 1 wherein the window element and mirror element are releasably secured to the ends of the cell body by at least three support rods.

4. A TGA/IR sampling apparatus comprising:
(a) a radiation source for projecting an infrared radiation beam;
(b) a TGA/IR flow cell interface comprising an elongated tubular cell body having first and second ends, and a wall defining an internal bore; inlet and outlet transfer lines connected to the cell body, the inlet and outlet transfer lines having channels in communication with the cell body bore for flowing a gas sample therethrough; an infrared transmissive window element mounted at one end of the cell body for allowing passage of the radiation beam into the and out of the bore of the cell body; and a mirror element mounted at the second end of the cell body for reflecting and directing a radiation beam back through the window element, wherein the TGA/IR flow cell interface is a single, readily removable assembly, thereby being readily adapted to be removed from the sampling apparatus;
(c) a system of transfer optics receiving the beam from the source and directing it through the window element and receiving a beam transmitted out of the cell body bore through the window element and redirecting the beam;
(d) a thermogravimetric analysis system connected to the inlet transfer line, the system producing a sample gas for analysis; and
(e) an oven compartment housing the interface unit and the system of transfer optics to provide a proper heated environment sufficient to prevent any condensation on the interface unit and system of transfer optics.

5. A TGA/IR sampling apparatus comprising:
(a) a radiation source for projecting an infrared radiation beam;
(b) a TGA/IR flow cell interface comprising an elongated tubular cell body having first and second ends, and a wall defining an internal bore; inlet and outlet transfer lines connected to the cell body, the inlet and outlet transfer lines having channels in communication with the cell body bore for flowing a gas sample therethrough; an infrared transmissive window element mounted at one end of the cell body for allowing passage of the radiation beam into and out of the bore of the cell body; and a mirror element mounted at the second end of the cell body for reflecting and directing a radiation beam back through the window element;
(c) a system of transfer optics receiving the beam from the source and directing it through the window element and receiving a beam transmitted out of the cell body bore through the window element and redirecting the beam;
(d) a thermogravimetric analysis system connected to the inlet transfer line, the system producing a sample gas for analysis; and
(e) an oven compartment housing the interface unit and the system of transfer optics to provide a properly heated environment sufficient to prevent any condensation on the interface unit and system of transfer optics, wherein the inlet and outlet transfer lines lead to positions outside the oven, where they will be at a lower temperature and are connected with normal supply and exhaust lines.

6. A TGA/IR sampling apparatus comprising:
(a) a radiation source for projecting an infrared radiation beam;
(b) a TGA/IR flow cell interface comprising an elongated tubular cell body having first and second ends, and a wall defining an internal bore; inlet and outlet transfer lines connected to the cell body, the inlet and outlet transfer lines having channels in communication with the cell body bore for flowing a gas sample therethrough; an infrared transmissive window element mounted at one end of the cell body for allowing passage of the radiation beam into and out of the bore of the cell body; and a mirror element mounted at the second end of the cell body for reflecting and directing a radiation beam back through the window element;
(c) a system of transfer optics receiving the beam from the source and directing it through the window element and receiving a beam transmitted out of the cell body bore through the window element and redirecting the beam;
(d) a thermogravimetric analysis system connected to the inlet transfer line, the system producing a sample gas for analysis; and
(e) an oven compartment housing the interface unit and the system of transfer optics to provide a properly heated environment sufficient to prevent any condensation on the interface unit and system of transfer optics, wherein the inlet line is not actively heated, thus permitting portions of heavier molecular weight bulk materials which may be present in the gas sample to condense in the inlet line.

7. An easily assembled and disassembled flow cell assembly for use in infrared spectrometry, comprising:
(a) an elongated tubular glass cell body having first and seconds ends, and a wall defining an internal bore;
(b) glass inlet and outlet transfer lines integrally fused to the cell body, the inlet and outlet transfer lines including channels for flowing a gas therethrough in such a manner that the channels communicate directly with the internal bore of the cell body;
(c) a window element for allowing passage of an infrared radiation beam into and out of the cell body, the window element mounted at the first end of the cell body, the window element including an infrared transmissive window bordered on either side by elastomeric sealing rings and nested within a window holder;
(d) a mirror element for reflecting the radiation beam, the mirror element mounted at the second end of the cell body, and an elastomeric sealing ring located between the cell body and the mirror element to sealingly engage the mirror element to the cell body; and (e) means for releasably securing the window element and mirror element to the cell body, wherein the means for releasably securing the window element and mirror element comprises a plurality of support rods having first and second ends, the first end of each rod releasably secured to the window element and the second end releasably secured to the mirror element.

8. The flow cell assembly of claim 7 wherein the support rods are each provided with a spring mechanism calibrated to provide the correct sealing force to the entire flow cell assembly.

9. A method of analyzing the effluent gas from a thermogravimetric analyzer with an infrared spectrometer, comprising:

(a) passing the effluent gas from the thermogravimetric analyzer to a TGA/IR interface system, the interface system comprising an elongated tubular cell body having first and second ends, a longitudinal axis and a wall defining an internal bore, inlet and outlet transfer lines connected to the cell body, the inlet and outlet transfer lines having channels for flowing the effluent gas therethrough, a window element for allowing passage of an infrared radiation beam into and out of the bore of the cell body, the window element being located at the first end of the cell body, and a mirror element for reflecting the radiation beam, the mirror element being located at the second end of the cell body, wherein the interface system is heated to substantially prevent condensation on the system, wherein the inlet transfer line, cell body, window element, mirror element, and the output transfer line define a gaseous flow path;

(b) passively heating the inlet transfer line by superheated gases flowing from the thermogravimetric analyzer;

(c) heating the flow path to prevent condensation of the effluent gas;

(d) directing the infrared radiation beam through the window of the interface system along an input pathway to the mirror element, wherein the radiation beam is reflected from the mirror element along an outlet pathway back through the window, such that the radiation beam traverses the longitudinal axis of the cell body twice, wherein the radiation beam interacts with the effluent gas; and (e) analyzing the radiation beam which is reflected back through the window, the radiation beam having interacted with the effluent gas.

* * * * *